(12) United States Patent
Tümer

(10) Patent No.: US 6,448,560 B1
(45) Date of Patent: *Sep. 10, 2002

(54) METHOD AND APPARATUS FOR GAMMA RAY DETECTION

(75) Inventor: Tümay O. Tümer, Riverside, CA (US)

(73) Assignee: Tumay O. Tumer, Riverside, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,144

(22) Filed: Jul. 20, 1998

Related U.S. Application Data

(63) Continuation-in-part of application No. 08/784,176, filed on Jan. 15, 1997, now Pat. No. 5,821,541.
(60) Provisional application No. 60/011,135, filed on Feb. 2, 1996.

(51) Int. Cl.$^7$ ................................................. G01T 1/24
(52) U.S. Cl. ................................................. 250/370.09
(58) Field of Search ................................... 250/370.09

(56) References Cited

U.S. PATENT DOCUMENTS

| | | | |
|---|---|---|---|
| 4,529,882 A | * 7/1985 | Lee | 250/363.1 |
| 4,857,737 A | 8/1989 | Kamae et al. | |
| 5,567,944 A | 10/1996 | Rohe et al. | |
| 5,821,541 A | * 10/1998 | Tümer | 250/370.09 |

OTHER PUBLICATIONS

Solomon, Christopher J. et al., "Gamma Ray Imaging with Silicon Detectors—A Compton Camera for Radionuclide Imaging in Medicine", *Nuclear Instruments and Methods in Physics Research* A273 (1988) pp 787–792.

Alpar, A., et al., "Tracking and Imaging Gamma Ray Experiment (TIGRE) for 1 to 100 MeV Gamma Ray Astronomy", *Tr.J. of Physics* vol. 18 (1994), pp 878–885.

O'Neill, T.J. et al., "Compton Recoil Electron Tracking with Silicon Strip Detectors", *IEEE Transactions on Nuclear Science*, vol. 39, No. 4 (1992) pp 629–634.

McKisson, J.E., et al., "Event–Restricted Monte Carlo Situations for Compton Telescope Image Reconstruction Studies", © 1993 *IEEE* 0–7803–0883–2/93, pp 667–669.

Martin, J.B., et al. "A Ring Compton Scatter Camera for Imaging Medium Energy Gamma Rays", ©1993 *IEEE* 0–7803–0883–2/93, pp 58–60.

Kamae, T., et al. "A new Method to Measure Energy, Direction, and Polarization of Gamma Rays", *Nuclear Instruments and Methods in Physics Research*, A260 (1987), pp 254–257.

Phillips, Gary W., "Gamma–Ray Imaging with Compton Cameras", *Nuclear Instruments and Methods in Physics Research*, B99 (May 1995), pp 674–677.

(List continued on next page.)

Primary Examiner—Constantine Hannaher
(74) Attorney, Agent, or Firm—Ronald R. Snider; Snider & Associates

(57) ABSTRACT

A high sensitivity, three-dimensional gamma ray detection and imaging system is provided. The system uses the Compton double scatter technique with recoil electron tracking. The system preferably includes two detector subassemblies; a silicon microstrip hodoscope and a calorimeter. In this system the incoming photon Compton scatters in the hodoscope. The second scatter layer is the calorimeter where the scattered gamma ray is totally absorbed. The recoil electron in the hodoscope is tracked through several detector planes until it stops. The x and y position signals from the first two planes of the electron track determine the direction of the recoil electron while the energy loss from all planes determines the energy of the recoil electron.

32 Claims, 8 Drawing Sheets

OTHER PUBLICATIONS

Tümer et al.; "A New Telescope for Wide–Band Gamma–Ray Astronomy: The Silicon Compton Recoil Telescope (SCRT)," *The Astrophysical Journal Supplement Series;* 92:671–674 (Jun. 1994).

O. T. Tümer et al.; "The TIGRE Instrument for 0.3–100MeV Gamma–Ray Astronomy," *Transactions on Nuclear Science,* vol. 42, No. 4 (Aug. 1995) pp. 907–916.

Farid Ait–Quamer et al.; "Calibration and Performance of the UCR Double Compton Gamma Ray Telescope," *IEEE Transactions on Nuclear Science,* vol. 37, No. 2 (Apr. 1990), pp. 535–540.

Tümer et al., "A High Sensitivity, Electronically Collimated Gamma Camera," *IEEE Transactions on Nuclear Science,* vol. 44, No. 3 (Jun. 1997), pp. 899–904.

* cited by examiner

METHOD AND APPARATUS FOR GAMMA RAY DETECTION

CROSS-REFERENCES TO RELATED APPLICATIONS

This application is a continuation-in-part of the U.S. application Ser. No. 08/784,176, filed Jan. 15, 1997 which is now the U.S. Pat. No. 5,821,541 and which claims the benefit of the U.S. Provisional application Ser. No. 60/011, 135, filed Feb. 2, 1996.

GOVERNMENT RIGHTS NOTICE

This invention was made with U.S. Government support under Contract Numbers R4MH49923 and DAMD17-96-1-6256 awarded by the Department of Health and Human Services and the Department of Defense, respectively. The U.S. Government has certain rights in the invention.

FIELD OF THE INVENTION

The present invention relates generally to detection systems, and more particularly, to a method and apparatus for imaging gamma rays.

BACKGROUND OF THE INVENTION

The various organs and tissues of the human body fall prey to a myriad of different afflictions. For example, each year in the United States alone, approximately 180,000 women are diagnosed with breast cancer and 46,000 women die of this disease. In all, 10 to 11 percent of all women can expect to be affected by breast cancer at some time during their lives. The causes of most breast cancers are not yet understood. Screening and early diagnosis are currently the most effective ways to reduce mortality from this disease.

Currently mammography is the most effective means of detecting non-palpable breast cancer. However, mammography cannot determine whether a lesion is benign or cancerous, typically one or more biopsies must be performed per lesion. Unfortunately the biopsy operation itself is a very traumatic and costly operation that often results in some degree of disfigurement. Therefore it is important to improve the specificity of mammography thereby reducing errors, patient trauma, and disfiguration from unnecessary biopsies. It is also important to reduce health care costs by decreasing the number of unnecessary biopsies. For example, to detect 100,000 non-palpable cancers, approximately 500,000 biopsies must be performed at a cost of about $5,000 per biopsy, yielding a total cost of approximately 2.5 billion dollars. Therefore a reduction of 50 percent would save about 1.25 billion dollars per year.

Palpable mass abnormalities of the breast are often difficult to evaluate mammographically. This is especially true for patients with dense or dysplastic breasts (approximately 35 percent of women over 50 and 70 percent of women under 50) or those patients that exhibit signs of a fibrocystic change, for example due to radiation therapy. For example, invasive lobular carcinoma in dense breasts can attain a size of several centimeters and yet still show no mammographically detectable signs. Furthermore, about 50 percent of all preinvasive cancers do not show mammographically significant calcifications, thus decreasing the chances of detecting the malignant tumors.

Lastly, due to the interpretational limitations of mammography, many high risk patients (i.e., patients with a family history of breast cancer, patients with prior histologic evidence of cellular atypia, patients with a prior history of breast cancer who have undergone lumpectomy and radiation therapy) may be forced to rely on random tissue biopsies performed on suspicious areas. Unfortunately this technique typically results in a high nonmalignant-to-malignant biopsy ratio.

A relatively new scientific tool that has allowed scientists and physicians to address problems in physiology and biochemistry in the human body with low risk is emission computed tomography (ECT). ECT systems are mainly used for the detection and imaging of the radiation produced by radiotracers and radiopharmaceuticals. For example, by administering biologically active radiopharmaceuticals into a patient it is possible to image organ functions in real time.

The two major instruments presently used for ECT are Single Photon Emission Computed Tomography (SPECT) and Positron Emission Tomography (PET). These instruments have been used to study a variety of different organs and conditions including cerebral glucose consumption, protein synthesis evaluation, cerebral blood flow and receptor distribution imaging, oxygen utilization, stroke, heart, lung, epilepsy, breast cancer, dementia, oncology, pharmacokinetics, psychiatric disorders, and radio labelled antibody and cardiac studies. Since the SPECT and PET instruments use different types of radiotracers, the metabolic activities imaged are mostly different leading these two instruments to complement rather than compete with each other. The SPECT detectors have proven especially useful for heart and brain imaging.

SPECT dates back from the early 1960s, when the first transverse section tomographs were presented by Kuhl and Edwards (1963) using a rectilinear scanner and analog back-projection methods. With the availability of computer systems and the impetus of computer-assisted tomography using transmitted x-rays, nuclear medicine instruments were modified, and a number of mathematical approaches to tomographic reconstruction were developed in the early 1970s. Rotating Anger cameras and advances in computers opened the way to three-dimensional SPECT systems. Recently interest in SPECT increased as mathematical reconstruction techniques improved. They allowed for attenuation compensation, scattered radiation correction and the availability of new radiopharmaceuticals with higher uptake in the brain or other organs. The major limiting factors for the SPECT systems presently are the sensitivities ($\approx$10 Cts s$^{-1}$ $\mu$Ci$^{-1}$ point and $\approx$1,000 Cts s$^{-1}$ cm$^{-1}$ volume), resolution (7 to 12 mm FWHM), size, and cost.

Present SPECT systems mainly use the rotating Anger camera. Many different variations of the Anger camera and other smaller size rotating single or dual instruments have been designed and used. Most of the commercial instruments use NaI(Tl), CsI(Tl), CsF, BaF$_2$, BGO and other related crystal detectors. The majority of the commercial instruments use the Anger cameras made of NaI(Tl) crystals. All commercial SPECT instruments use collimators for determination of the direction of the incident gamma rays. The main types are parallel and converging collimators. The converging fan or cone beam collimators produce higher sensitivity but increase the complexity of the data analysis. Pinhole and slit collimators are also used. The collimators for high resolution systems eliminate about 99.9 percent of the incident gamma rays. A typical collimator hole has an area of about 1 square millimeter and a length of 1.9 centimeters. Increasing collimator resolution decreases sensitivity and vice versa. Collimators made of high atomic number materials such as lead which also produce considerable amounts of scattered gamma rays on the inside surface of the collimator, thereby increasing the scattered photon background.

Anger cameras are normally rotated on a gantry around the patient for about 20 minutes to acquire sufficient data for a reasonable image. The spatial resolutions are limited to about 7 to 12 millimeters although spatial resolutions are expected to reach 6 millimeters in the near future. The best energy resolution at gamma ray energies is about 10 percent, limiting the ability of Anger cameras to discriminate scattered photon background. Commercially available SPECT systems include ADAC ARC, GE Starcam, Elscint APEX, Trionix Triad, Digital Scintigraphics ASPECT and University of Michigan SPRINT II.

From the foregoing it is apparent that an improved gamma ray imaging system is desired.

SUMMARY OF THE INVENTION

The present invention provides a high sensitivity, high spatial resolution, and electronically collimated single photon emission computed tomography (SPECT) system. Its primary sensitivity is in the range of 81 keV to 511 keV although it can be used to detect higher energies of up to a few MeV by increasing the detector thickness for both the hodoscope and the calorimeter. Both the direction and energy of the incident gamma ray photons is measured with high resolution. The method of determination of the photon direction eliminates the need for a mechanical collimator and the energy measurement discriminates against the scattered photon background.

The disclosed system is constructed from position sensitive, double sided silicon strips with a strip pitch of approximately 1 millimeter or silicon microstrips with a strip pitch much less than a millimeter. Preferably the system uses the silicon strip detectors. These detectors, varying in thickness from 150 micrometers to 2 millimeters, can produce the x and y coordinates of a photon interaction in a single wafer.

One embodiment of the system uses multiple planes of double sided silicon strip detectors with about 1 millimeter pixel size and a thickness of 100 micrometers to 5 millimeters. The planes are separated by a distance of between 0.2 and 2 centimeters, depending on the pixel size and the required angular resolution. The smallest possible separation is always preferred to keep the depth of the detector small without sacrificing spatial resolution. The incident gamma ray Compton scatters in one of the detector planes, the dominant process for photons with at least 50 keV energies in silicon strip detectors. The energy of the scattered electron in this detector plane is measured. The scattered gamma ray with reduced energy can be absorbed in the calorimeter or in an another detector plane through the photoelectric effect or undergo multiple Compton scatters followed by a photoelectric effect. The energies of these subsequent interactions are also measured. If the scattered gamma ray photon is completely absorbed, the sum of the two energies gives the energy of the incident photon and the individual energies and direction of the scattered photon give the scatter angle of the incident gamma ray. Thus the gamma rays emitted from a radionuclide can be imaged without need for a collimator.

The scattered gamma ray photons can make a second Compton scatter and then escape without further interaction. Also the photons already scattered inside the patient will deposit lower total energy. These events will produce a tail at lower energies in the energy spectrum. Such events can be discriminated effectively because the total energy detected is smaller than the known incident gamma ray energy. However, a high sensitivity mode may be applied with reduced angular resolution by adding the missing energy to the energy measured at the second scatter. This will dramatically increase the sensitivity but reduce angular resolution somewhat and will not allow the discrimination of the scattered photon background.

A calorimeter surrounding the silicon strip detector hodoscope absorbs the Compton scattered photons. The calorimeter can be fabricated from a plane of silicon a few millimeters thick, CdZnTe strip and/or detectors, or CsI(Tl) crystals viewed by a photodiode. The calorimeter can also be used as a second scatterer and/or a missing energy detector.

The double Compton scatter measurement determines the direction of the incident gamma ray to a cone with a half angle equal to the scatter angle. This type of measurement is new in nuclear medicine and requires special data analysis software. The data analysis can be carried out by cone interaction, Maximum Likelihood or Maximum Entropy techniques. These are iterative techniques and require long computation times. A new direct data analysis and imaging technique, Direct Linear Algebraic Deconvolution (DLAD) method, can also be applied for real time imaging.

In use, the present system utilizes the higher uptake of certain radiopharmaceuticals by the organ or tissue of interest, thereby allowing the selected organ/tissue to be imaged. For example, malignant tissues preferentially absorb Tc-99m SestaMIBI and Tl-201 chloride as compared to benign masses (except for some highly cellular adenomas). Therefore, these radiopharmaceuticals can be used to help diagnose and differentiate tumors from benign growths, for example in a scintimammography system for breast cancer detection and diagnosis. Possible mechanisms for uptake of Tl-201 chloride into tumor cells include the action of the ATPase sodium-potassium transport system in the cell membrane which creates an intracellular concentration of potassium greater than the concentration in the extracellular space. Thallium may be significantly influenced by this system in tumors. In addition, a co-transport system has been identified which also is felt to be important in uptake of thallium by tumor cells.

A further understanding of the nature and advantages of the present invention may be realized by reference to the remaining portions of the specification and the drawings.

DESCRIPTION OF THE SPECIFIC EMBODIMENTS

Gamma Ray Detection

The most probable interaction mechanism for 0.05 to 10 MeV gamma rays in silicon is the Compton scatter process. Therefore, the detection of gamma rays in this energy range must use Compton interaction to have maximum sensitivity. The detector must also have excellent angular and energy resolution and a wide field-of-view. The best detection technique that has all of these features is the Compton double scatter method. This technique incorporates Compton scattering, photoelectric absorption, and pair production. The three gamma ray interaction mechanisms are briefly discussed below.

Although a number of possible interaction mechanisms are known for gamma rays in matter, only three major types play an important role in radiation detection: photoelectric absorption, Compton scattering, and pair production. Of these, only the first two play a major role in emission imaging. All of these processes lead to the partial or complete transfer of the photon energy to electron energy. They result in sudden and abrupt changes in the photon history where the photon disappears entirely or is scattered through a significant angle.

Figure 1:
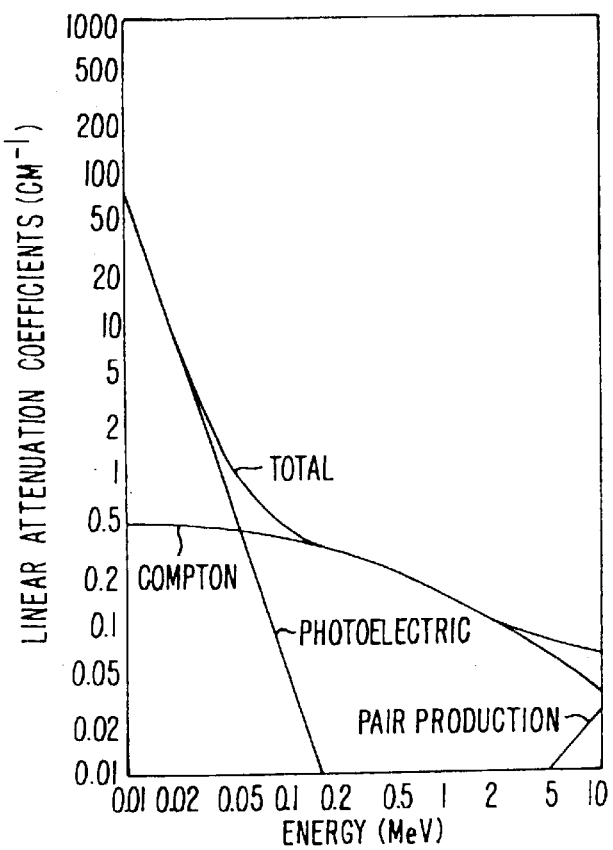
FIG. 1 is an illustration of the gamma ray linear attenuation coefficients for a silicon detector.

FIG. 1 is an illustration of the gamma ray linear attenuation coefficients for silicon microstrip detectors through these three processes. The photoelectric absorption dominates below about 50 keV for silicon. Compton scattering becomes important at about 50 keV and it stays the dominant process up to about 10 MeV, where pair production takes over. In the range of 81 to 511 keV which includes the nuclear medicine range, the important detection process for silicon is Compton scattering. Compton scattered gamma ray photons with energies less than 50 keV are readily absorbed due to the photoelectric effect.

In the photoelectric absorption process, a photon undergoes an interaction with an absorber atom in which the photon completely disappears. In its place, an energetic photoelectron is ejected by the atom from one of its bound shells. The interaction is with the atom as a whole and can not take place with free electrons. The photoelectron appears with an energy, $E_e$, given by $$E_e = h\upsilon - E_b$$

where $h\upsilon$ is the incident photon energy and $E_b$ represents the binding energy of the photoelectron in its original shell. For gamma ray energies, $h\upsilon$, of more than a 100 keV, the photoelectron carries off most of the original photon energy. For silicon microstrip detectors, this process is only important for low energy gamma rays in the range of 0.5 to 50 keV. Photoelectric absorption falls nearly exponentially with an increase in energy. Since the incident photon is totally absorbed it is not possible to determine the direction of the incident photon. Therefore collimators must be used to determine the direction of origin of the photon.

Figure 2:
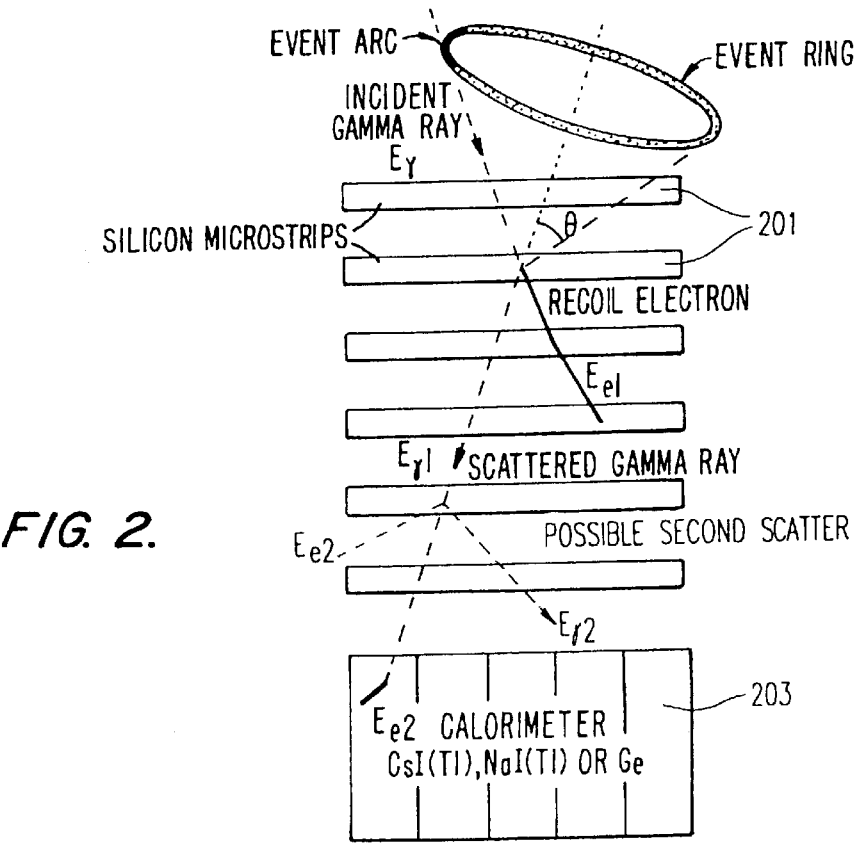
FIG. 2 is an illustration of the Compton scatter technique for detecting gamma rays.

Compton scattering takes place between the incident gamma ray and an electron in the absorbing material. In Compton scattering, the incident gamma ray is deflected through an angle θ with respect to its original direction as illustrated in FIG. 2. The photon transfers a portion of its energy to the recoil electron that was initially at rest. Because all angles of scattering are possible, the energy transferred to the electron can vary from zero to a large fraction of the gamma ray energy. This has been a problem in the detection of gamma rays at energies dominated by the Compton scatter process, since the detected recoil electron alone does not give sufficient information to uniquely determine the energy and direction of the incident photon. This has been solved by the Compton double scatter technique described below and illustrated in FIG. 2.

The total incident gamma ray energy, $E_\gamma$, and Compton scatter angle, θ, for the double scatter process are given by:

$$E_\gamma = E_{e1} + E_{\gamma 1}$$

and $$\cos\theta = 1 - mc^2(1/E_{\gamma 1} - E_\gamma)$$

The incident gamma ray first scatters by the Compton process in one of the silicon strip detectors 201, losing recoil energy $E_{e1}$. The scattered photon continues on until it interacts with another silicon strip detector or is absorbed by a calorimeter 203. If the second interaction is photoelectric absorption, the full energy of the scatter photon is measured and the energy of the incident photon and the scatter angle are determined. This is the dominant process for the calorimeter as it is made of high Z material and photoelectric absorption increases exponentially with a decrease in the scattered photon energy. Another possibility is that the second interaction can be another Compton scatter where the photon escapes with a small amount of the energy. If the energy of the escaping photon is sufficiently low, the energy determination is not significantly effected. If there are enough silicon planes, the escaped photon makes further interactions in subsequent planes and gets fully absorbed by the photoelectric effect. All of the energy measured after the second scatter is just added to the energy of the second scatter, $E_{e2}$, to correct for the missing energy. If not enough silicon planes are used, for example due to cost considerations, a calorimeter can be placed such that it surrounds the sides and the bottom of the silicon strip detector hodoscope. The surrounding calorimeter is used as a second scatterer to measure the energy and direction of the scattered photon or to catch the escaping photons and correct $E_{e2}$ for accurate incident photon scatter angle determination. Since the calorimeter is a high Z and high density detector or scintillator, there is a high probability that the escaped low energy photon will be fully absorbed. The events that do not add up to the full energy of the incident photon are rejected to reduce scattered photon background.

The incident gamma ray direction lies on a cone segment in the field-of-view with a half-angle θ. The cone axis is determined by the interaction positions in the first and the second scatters. This is because the direction of the scattered electron in the top scintillator is not measured. The Compton scattered electrons with energies in the range of 81 to 364 keV are fully stopped within 0.03 and 0.3 millimeters of the silicon strip detectors, respectively. Therefore silicon strip detectors with a thickness of 0.3 to 2 millimeter are ideal for the present system.

Silicon Microstrip Detectors

In the preferred embodiment of the invention, silicon microstrip detectors are used as the first scatterer (i.e., hodoscope). Silicon microstrip detectors have large active areas, excellent energy and position resolution, and fast readout. Three inch diameter wafers, typically 200 to 500 micrometers thick, with parallel readout strips of greater than 25 micrometers pitch on one side have been available for few years. Pitch size can have any value from 25 micrometers to several centimeters.

On the average, 1 electron-hole pair is produced per 3.6 eV of deposited energy. The energy deposited by an 80 keV recoil electron fully stopped in silicon is about 22,000 electrons (and holes) which can be collected in less than 10 nanoseconds. This leads to pulse rise times of less than 10 nanoseconds. Spatial resolutions of less than 10 micrometers in one dimension are obtainable by exploiting charge division between adjacent strips. Superimposed on the signal is Gaussian-distributed noise related to the detector strip and preamplifier input capacitances. This noise or equivalent noise charge (e.g., ENC) is typically about 1,000 electrons at room temperature for detector capacitances of about 20 pF. Thus large signal-to-noise ratios, on the order of 22, are obtainable for 80 keV electrons.

To date, silicon detectors have been primarily used in high energy physics experiments to detect minimum ionizing high energy charged particles. The Compton converter in the present invention is different in that the recoil electron loses its entire energy in a single detector wafer of about 1 millimeter thickness instead of depositing only part of its energy like the minimum ionizing particles. The energy and angular resolutions improve as the number of electron-hole pairs created in the silicon increase. For a 300 keV recoil electron stopping in silicon, about 83,000 electrons (i.e., 278 e/keV) are produced with an inherent energy resolution of 0.8 percent (i.e., $FWHM/E_0 = 2.35/\sqrt{N}$ where N is the number of electron-hole pairs). For 141 keV electrons stopping inside the silicon wafer, the theoretical energy resolution is calculated to be about 1.2 percent with a stopping distance for the recoil electron of about 0.1 millimeters. The theoretical resolution can be approached if the input capacitance and the preamplifier noise can be kept low. The input capacitance can be decreased substantially by mounting the chips next to the strips or building them on the same silicon. In the present invention a low noise, 64 channel front end mixed signal application specific integrated circuit (ASIC) readout chips is used.

The individual detector thicknesses can be increased in order to decrease the number of required planes. Silicon strip detectors with a 1 millimeter thickness are readily available while detectors with thicknesses of 2 millimeters have been manufactured. The energy resolution of silicon strip detectors is a dramatic improvement over scintillators (e.g., BC-523: 17% at 0.5 MeV).

Figure 3:
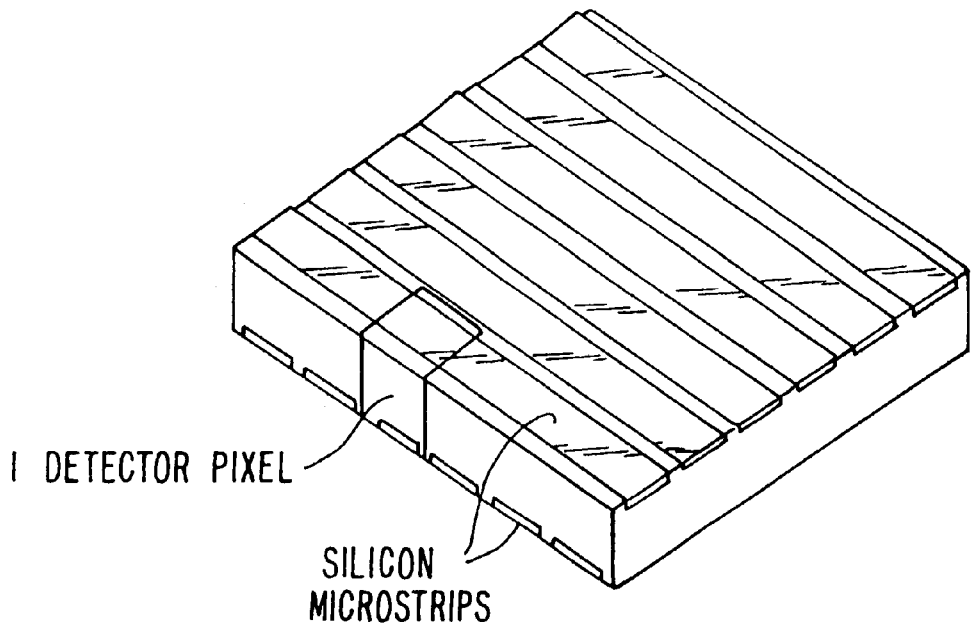
FIG. 3 is an illustration of a typical double sided silicon microstrip or strip detector.
Figure 4:
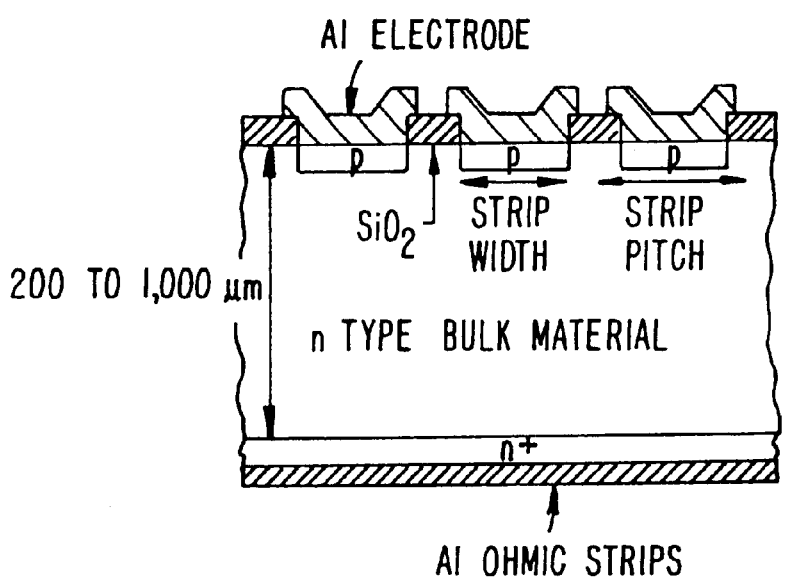
FIG. 4 is the schematic cross section of the detector illustrated in FIG. 3.

Double sided readout silicon microstrip detectors with orthogonal strips on opposite sides have been developed. FIGS. 3 and 4 show the basic features of a double sided silicon microstrip or strip detector. The distinct advantage with this configuration is that both x and y coordinates of a traversing particle are determined in a single detector plane. For single sided detectors, the junction side of a standard p+n diode is segmented into many strips. For double sided detectors, the ohmic side of the n-type silicon wafer is also segmented with orthogonal strips to provide simultaneous readout of the particle impact point. Position resolutions well below a square millimeter on both sides can be achieved. The preferred detector in the present invention uses 200 to 300 micrometer thick, double sided, silicon microstrip detectors with about a millimeter spaced strips orthogonal on the top and bottom surfaces. Such detectors are now commercially available and fit well with the present design. The x and y positions of the first two interaction points on the recoil electron track determine the electron direction. A combination of all interactions is used to determine the energy of the recoil electron as well as the scatter angle.

In one embodiment of the invention, the detector is 6.4 centimeters by 6.4 centimeters, the detector being fabricated from a 4 inch wafer. In another embodiment, 10 centimeter by 10 centimeter detectors are used. Bridged detectors with overall lengths exceeding 25 centimeters can also be used with the present invention. Bridging allows one preamplifier to be connected to a series of strips on adjacent detectors with significant savings in electronics.

A simple Monte Carlo calculation using Monte Carlo Neutron Photon (MCNP) software from Los Alamos National Laboratory was performed. The MCNP software gives the probability for a 141 keV photon to Compton scatter in varying total silicon thicknesses. For example, about 50 percent of the 141 keV photons will Compton scatter in a silicon detector 2 centimeters thick. If 2 millimeter thick silicon strip detectors are used, then 10 planes will be required. For lower energy photons, a lower total thickness is required.

Another important advantage of silicon microstrip detectors is that they do not need high voltages or cooling to low temperatures. Room temperature functionality is important to produce small size, low cost, and low power detectors. They also have a strong potential for mass production. However, a significant number of wafers are needed to achieve the conversion rates required for high sensitivity. Their small thickness and ultrasonic wire bonding capability render them good candidates for compact printed circuit board mounting with data acquisition ICs placed next to them. The readout ICs are preferably designed to give fast trigger outputs when events occur and output the address and the analog content of the channel that has the data.

Calorimeter

Preferably a calorimeter is placed around and at the bottom of the silicon microstrip detectors in order to absorb the escaping Compton scattered photons. A variety of different high density radiation detectors can be used. Many of these detectors are relatively high cost (e.g., HPGe, BGO, $CdWO_4$ and CsF) and several require cooling to liquid nitrogen temperatures (e.g., HPGe).

Sodium Iodide is the most popular high density scintillator. It has a large light yield and its response to electrons and gamma rays is close to linear over most of the significant energy range. The NaI(Tl) crystal is fragile and hygroscopic and therefore must be handled carefully and hermetically sealed. It has long decay time and is not suitable for fast timing applications.

Cesium Iodide is another alkali halide that has gained substantial popularity as a scintillator material. It is commercially available with either thallium or sodium as the activator material and has significantly different scintillation properties with thallium. CsI has a larger gamma ray absorption coefficient per unit size and is less brittle than NaI. The two forms of CsI scintillators, CsI(Na) and CsI(Tl), are discussed separately below.

CsI(Na) has an emission spectrum similar to NaI(Tl). Its light yield is also comparable. CsI(Na) is hygroscopic and must be hermetically sealed. Therefore, CsI(Na) is similar to NaI(Tl) and has the same draw backs.

CsI(Tl) is different than NaI(Tl) and has unique properties. It is also only slightly hygroscopic. Energy resolution of 5 percent FWHM at 0.662 MeV has been obtained with 2.5 centimeter diameter by 2.5 centimeter thick CsI(Tl) scintillation crystals coupled to large area (e.g., 2.5 centimeter diameter) mercuric iodide photodetectors. This is about 50 percent better than the NaI(Tl) detectors. The mercuric iodide photodiodes are not yet available as commercial devices. Resolution of 6 percent at 0.662 MeV has been obtained for considerably smaller CsI(Tl) crystals using avalanche photodiodes. Large area PIN diodes coupled to 1 centimeter by 2 centimeter CsI(Tl) crystals give a 7 percent resolution at 0.662 MeV. These crystals produce 35 percent more photons per MeV than NaI(Tl) and their light spectrum is much better matched to the sensitivities of the photodiodes. A key to improved energy resolution is good light collection by matching the areas of the crystals to those of the photodiodes.

Figure 5:
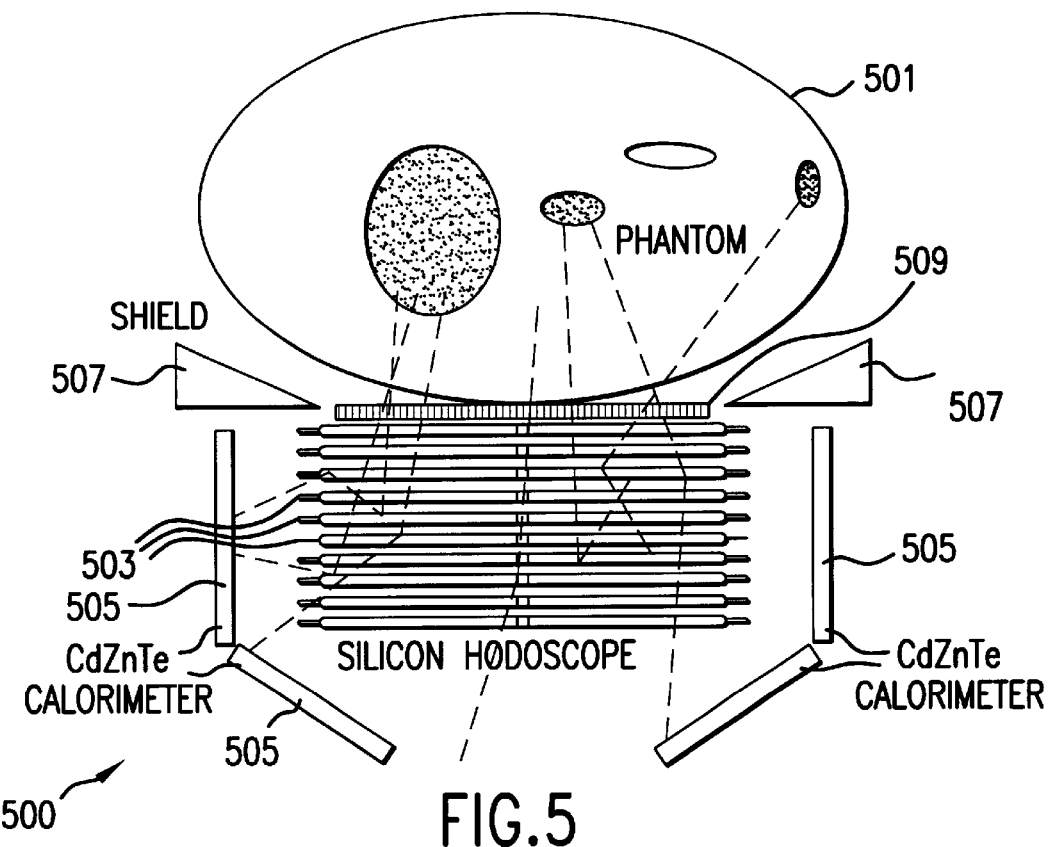
FIG. 5 is an illustration of a side view of an embodiment of the invention.

An important property of CsI(Tl) is its variable decay time for different particles. Therefore pulse shape discrimination techniques can be used to differentiate among various types of radiation such as electrons, protons and alpha particles. The CsI(Tl) light output is quoted lower than NaI(Tl) for bialkali photomultiplier tubes (PMTs) (FIG. 5). The scintillation yield is actually found to be larger than that of any other scintillator because its light emission peaks at longer wavelengths. It can be used with photodiodes with extended response in the red region of the spectrum. Its energy resolution is equal to or better than the energy resolution of the NaI(Tl) crystals. For these reasons CsI(Tl) crystals are used in at least one embodiment of the invention.

CdTe, CdZnTe, HPGe and $HgI_2$ are solid state detectors and can be made in arrays for position sensitive applications. They are high Z and high density crystals. They are used to detect x-rays and gamma rays directly without need for photomultiplier tubes or PIN and avalanche photodiodes. They produce much better energy resolution than the other detectors which require photomultiplier tubes or PIN and avalanche photodiodes since they convert the energy deposited by the x-ray and gamma ray photons into light, not electron-hole pairs.

High purity germanium (HPGe) offers excellent high energy resolution and exhibits moderate gamma ray absorption properties, making it the detector of choice for high accuracy spectroscopy. Unfortunately since it only works at liquid nitrogen temperatures, bulky refrigeration systems are required which further increase the cost of this detector. HPGe is available in single small crystals and works by collecting the electron hole pairs produced inside the crystal similar to the silicon detectors and does not require PMTs. Because of the large cost this detector is mainly used for applications which require ultra high energy resolution and small size detectors.

BGO, $CdWO_4$ and CsF are excellent high density and high Z scintillators. They have lower energy resolution and light output. Their maximum light emissions peak around 430 nanometers, similar to NaI(Tl), and require PMTs for detection. $CdWO_4$ and especially CsF have shorter decay constants and faster rise times than the others and can be used for timing. However, since the preferred detector of the present invention does not use time-of-flight to determine the direction of the scattered gamma ray photon, good time resolution is not important.

The preferred room temperature detector for the calorimeter of the present invention is CdTe or CdZnTe. These detectors are described in more detail below.

System

The present invention, relying on isotope uptake in the region (i.e., organ or tissue) of interest, can be used for a variety of different applications ranging from real-time monitoring (e.g., blood flow through a heart valve) to lesion diagnosis (e.g., breast lesions). The disclosed system is relatively compact while offering improved efficiency and spatial resolution. An obvious benefit of the improved efficiency of the present invention is a significant decrease in the observation time or the radiopharmaceutical dosage.

Figure 6:
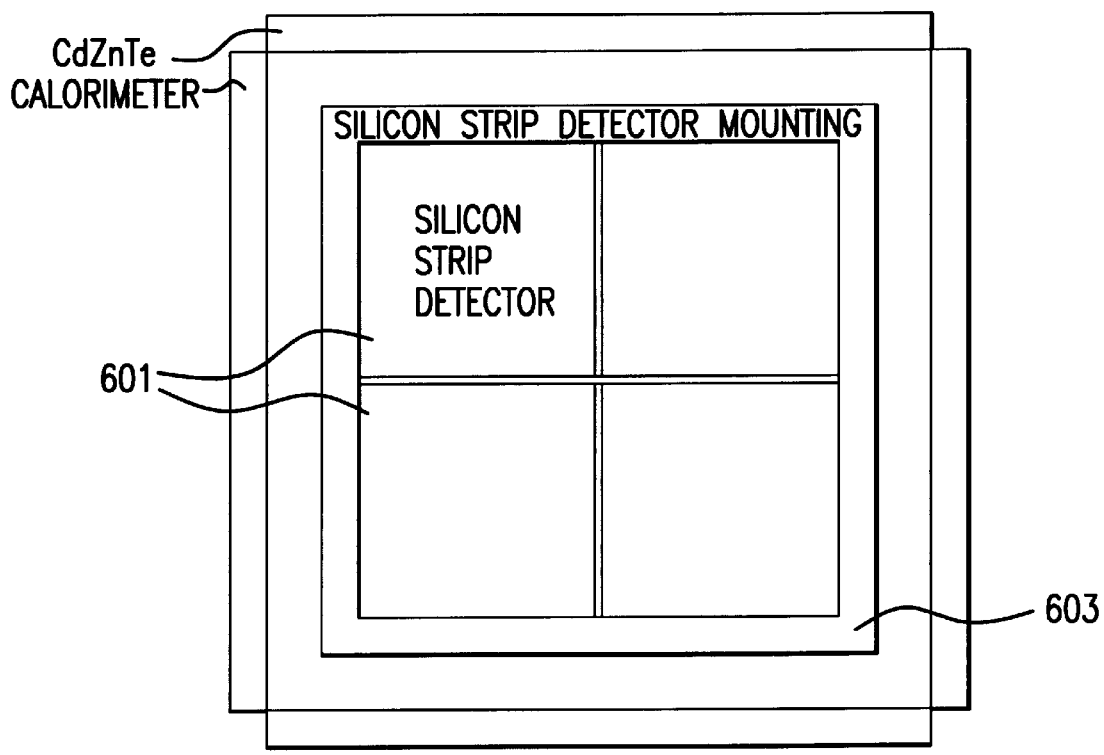
FIG. 6 is an illustration of a top view of the system illustrated in FIG. 5.

One embodiment of the invention is illustrated in FIGS. 5 and 6. An object 501 to be imaged such as a breast, brain, or other organ or tissue is placed at the front of system 500. The hodoscope is made up of between approximately 1 and 100, and preferably between approximately 10 and 25, silicon strip detector planes 503. Detector planes 503 preferably have a thickness of between 0.5 to 1 millimeter, the selected thickness being dependent upon the desired performance as well as the availability of the detectors. The total Compton scatter probability will vary from approximately 50 percent for ten 2 millimeter thick silicon strip detectors to approximately 35 percent for twenty five 0.5 millimeter thick detectors. The active area of the silicon strip detectors can be increased by mounting four or more detectors 601 side by side on each plane 503 as shown in FIG. 6.

The hodoscope height depends strongly on the number of detector planes 503 as well as the separation between the planes. In the illustrated embodiment, 1 millimeter thick detectors are used giving a plane separation of about 1 centimeter and a hodoscope height of about 15 centimeters. Preferably these values as well as the thickness and separation of the silicon detectors is optimized through Monte Carlo simulations and experimental study.

The calorimeter is made from about 2 millimeter thick CdTe or CdZnTe strip or pad detectors 505. The reason for this selection is the higher energy resolution obtained from CdTe/CdZnTe detectors especially at lower energies. A CsI(Tl) calorimeter can also be used.

In the illustrated embodiment, calorimeter 505 is a single layer placed around, and as close as possible, to the hodoscope. The proximity of the calorimeter to the hodoscope is limited in order to avoid introducing significant angular resolution degradation due to the geometric combination of pixels. The gap at the bottom is due to the energy threshold of the silicon detectors which is typically greater than 5 keV. The incident photons that deposit energy less than the threshold energy will not be detected in the hodoscope and such small angle scatters need not be stopped at the calorimeter. The geometry, strip pitch, thickness, shielding, and the size of the gap at the bottom of the calorimeter is optimized by Monte Carlo simulations. The detector geometry is optimized to any form such as square, rectangular, cylindrical, spherical, parabolic, etc. that gives the best results for a specific application.

A shield 507, preferably made of a material such as lead or tungsten, is placed in front of and around the calorimeter to reduce the background. Shield 507 is especially important for certain applications. For example, if imaging system 500 is used for the detection of malignant breast tumors, a radiopharmaceutical such as Tc-99m SestaMIBI or Tl-201 may be used. In either case, substantial amounts of the radiopharmaceutical may be taken in by the heart thus requiring adequate shielding to achieve the desired signal-to-noise ratio.

In an alternate embodiment used to obtain an intermediate improvement in sensitivity, a slot collimator 509 is placed at the aperture of the hodoscope. Collimator 509 confines photons to the planes defined by the slots. Collimator 509 will therefore slice the event cone inherent in a Compton scatter detector into two sections, one section defining the true event direction and the other section defining the false event direction. The false event directions normally lie outside the viewed object, especially for large scatter angles. Thus the correct and incorrect directions can be defined for each event and all false events can be rejected.

In the preferred embodiment of the invention, each plane of the hodoscope is made from four 1 millimeter thick silicon strip detectors 601 with an active area of approximately 6.4 centimeters by 6.4 centimeters each. Detectors 601 are mounted as close to each other as possible. Therefore in this embodiment the active area is approximately 12.8 centimeters by 12.8 centimeters or about 164 square centimeters. The number of detector planes 503 is a function of the application. For example, if system 500 is to be used to image breast tumors, the hodoscope preferably has 10 detector planes with a 0.5 centimeter spacing. For other organ imaging applications the hodoscope has between 15 and 25 detector planes with an approximately 1 centimeter spacing.

Figure 7:
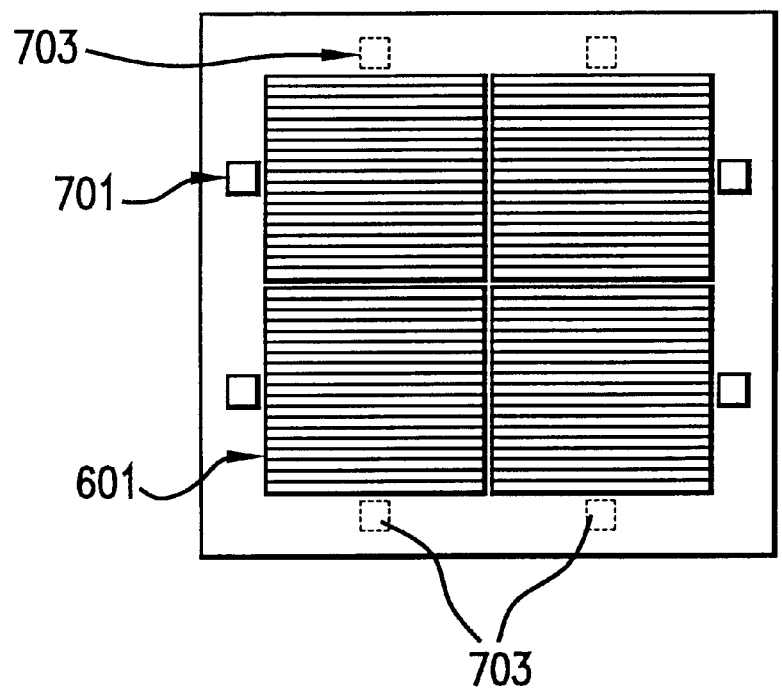
FIG. 7 is an illustration of the FEE readout chips and the silicon strip detector planes mounted on a printed circuit board.

Silicon strip detectors 601 are mounted on a printed circuit board (PCB) 603 or a ceramic holder as illustrated in FIGS. 6 and 7. Front end electronics (FEE) readout chips are mounted on the PCB proximate to the silicon strip detectors 601 either on the front surface of the PCB at locations 701 or on the back surface of the PCB at locations 703. A fan-in from the strip pitch to the FEE chip pad pitch is done on the silicon strip detector for reliability and ease of ultrasonic wire bonding.

Preferably silicon strip detectors 601 are designed and fabricated using the new FOXFET AC coupling technique on both the junction and ohmic sides. This technique improves the signal quality, especially at the ohmic side, since the bias resistor formed through the FOXFET technique is much larger than with other techniques. It also eliminates external capacitances and resistors which become bulky, require large real estate, and are costly when large numbers of channels are used. Preferably high radiation resistant FOXFET silicon strip detectors are used which significantly increases the reliability of the system.

FOXFET silicon strip detectors are commercially available and show excellent response to low energy (i.e., 81 to 511 keV) photons. By lowering the dark current and reducing the junction thickness to decrease strip capacitance, a reduction in detector and electronic noise should be achieved, thereby improving energy and spatial resolution.

The small size of the active area and the dividers between the four silicon strip detectors at each plane do not cause problems such as side truncation or image gaps. This is because the disclosed technique inherently has a large field of view and the detector active area can be smaller than the imaged organ of the patient. Smaller active area, dead strips within a plane, or gaps in between the silicon strip detectors, only reduce the detection efficiency while not affecting the image. Thus as a result of the Compton scatter technique, image defects are virtually eliminated due to the system's tolerance to defects.

Although the invention can be used without a calorimeter, the preferred embodiment includes a calorimeter utilizing CdZnTe strip detectors. These detectors have excellent energy resolution for 10 to 250 keV gamma rays, or for 250 to 600 keV gamma rays if thick detectors are used. Therefore, CdZnTe is especially useful to work with $^{99m}$Tc and $^{201}$Tl, the most commonly used radionuclides.

The second choice for the calorimeter are CsI(Tl) crystals coupled to specially developed PIN photodiodes. The energy resolution of these crystals, contrary to CdTe detectors, increases as the gamma ray energy increases. Therefore, they are an excellent choice for source gamma rays with energies greater than 250 keV.

At higher energies, the thickness of silicon required to stop the gamma rays becomes larger, requiring multiple Compton scatters prior to absorption. If a calorimeter is used, the incident photon only needs to make a single Compton scatter in the silicon hodoscope.

The energy resolution for a 1 by 1 by 2 cubic centimeter crystal of CsI(Tl) is approximately 5 percent at 662 keV using a $^{137}$Cs source, thus showing that a CsI(Tl) calorimeter can be used with the present invention. A CsI(Tl) calorimeter with smaller crystals can be used at lower energies without a significant impact on the stopping power of the calorimeter. For example, a 0.5 centimeter long CsI(Tl) crystal can absorb 95 percent of 141 keV photons.

In general the present invention has three basic embodiments depending upon the intended use. The first embodiment is intended for relatively low energy, i.e., between about 81 and about 250 keV. Due to the low energy, this embodiment can be fabricated either with or without a calorimeter. If a calorimeter is used, preferably it is a CdZnTe calorimeter. The second embodiment is intended for relatively high energy, i.e., between about 250 and about 511 keV or greater. This embodiment uses both the hodoscope and the calorimeter, the calorimeter utilizing either CdZnTe or CdI(Tl). The third embodiment can be used throughout the entire energy range, albeit with slightly lower efficiency and spatial resolution. In this embodiment preferably a CsI(Tl) or a thick (e.g., 0.5 to 1 centimeter) CdZnTe calorimeter is placed behind a 2 millimeter thick CdZnTe plane. The CdZnTe calorimeter is useful for low energy radionuclides while both the CdZnTe and the CsI(Tl) calorimeter can be used with the silicon hodoscope for high energy sources. In such an arrangement interactions in all three sections may happen and can be used as viable data for imaging.

The origin of CdZnTe is the cadmium telluride (CdTe) detector. CdTe contains relatively high atomic numbers (i.e., 48 and 52) with a large enough bandgap energy (i.e., 1.47 eV) to permit room temperature operation. This bandgap limits resistivities to the low-109 ohm-centimeter range, resulting in relatively large room temperature dark currents. CdTe has a density of 6.06 grams per cubic centimeter and the energy required to create a single electron-hole pair is 4.43 eV. The hole mobility is about a factor of 30 slower than the electron mobility. The hole life times are also very short due to the low mobility enhancing the effects of trapping and recombination. Improvements in hole collection efficiency can be obtained by using higher purity materials.

In CdTe, for typical gamma ray energies the probability of photoelectric absorption per unit pathlength is approximately 100 times larger than in silicon. For example, CdTe is opaque to low energy x-rays for thicknesses in the range of a millimeter. However, the energy resolution of CdTe is not comparable to silicon detectors for low energy x-rays due to poor hole collection efficiency. The room temperature measured energy resolution for CdTe detectors is 3.5 keV at 122 keV.

Many problems associated with CdTe detectors are related to a specific technique of crystal growth referred to as the traveling heater method (THM). This technique requires that the crystals be doped with an element such as chlorine in order to achieve high resistivity. Unfortunately, chlorine doping is generally associated with detector long-term reliability problems as well as various operating instabilities such as counting rate polarization. Lastly, due to the low yield of detector grade material using this technique, detector prices are relatively high.

The CdZnTe detectors were specifically developed as gamma ray detectors by several companies. By using a high pressure Bridgman (HPB) technique to grow the crystals, improvements in both size (e.g., up to 10 centimeter diameter crystals weighing over 10 kilograms) and yield (e.g., over 70 percent) have been realized. These crystals exhibit uniform, near-intrinsic resistivity without doping. Detectors fabricated from HPB grown crystals exhibit excellent stability, reliability and lifetime. Furthermore, the HPB process can be used to grow high quality crystals of $Cd_{1-x}Zn_xTe$ throughout the entire alloy composition range. Alloying ZnTe with CdTe increases the bandgap, resulting in much higher resistivities and correspondingly lower leakage currents than CdTe.

Figure 8:
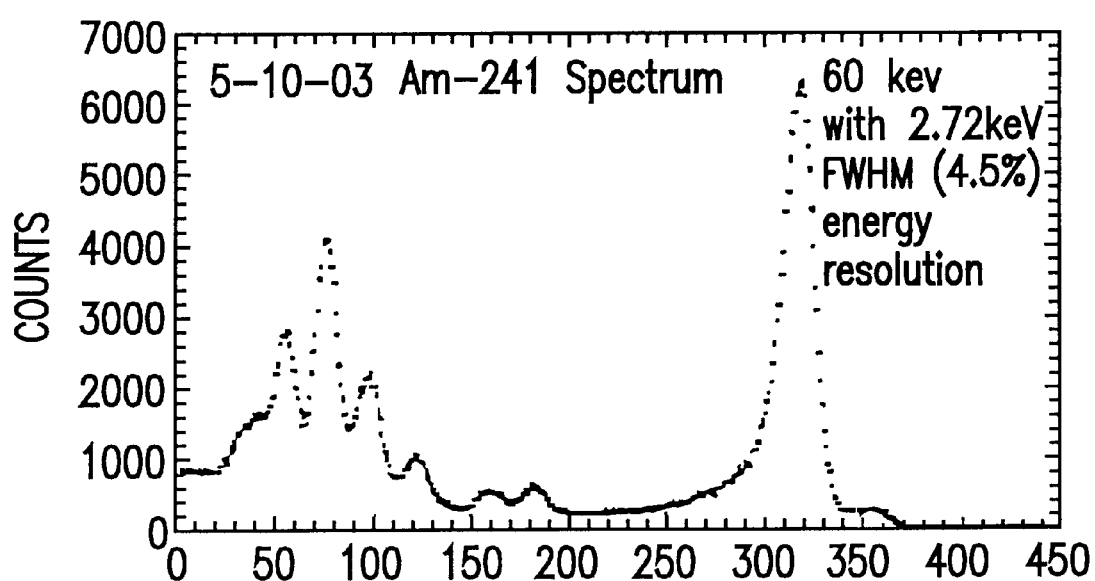
FIG. 8 is a graph illustrating the energy spectrum of Americium-241 using a CdTe detector.

The energy resolution of both the CdTe and CdZnTe detectors for 10 to 300 keV energies is important for the present invention. FIG. 8 shows the energy spectrum of an Americium-241 source with a CdZnTe detector. The x-ray emissions at 13.9, 17.7, 20.8, 26.4, and 59.5 keV (with escape peaks for characteristic K x-rays from Cd at 36.5 keV and Te at 32.5 keV) are clearly seen with good energy resolution. The slightly lower energy tail observed for the 59.5 keV peak is typical of that observed with CdZnTe detectors and is due to incomplete charge collection for some of the events.

Figure 9:
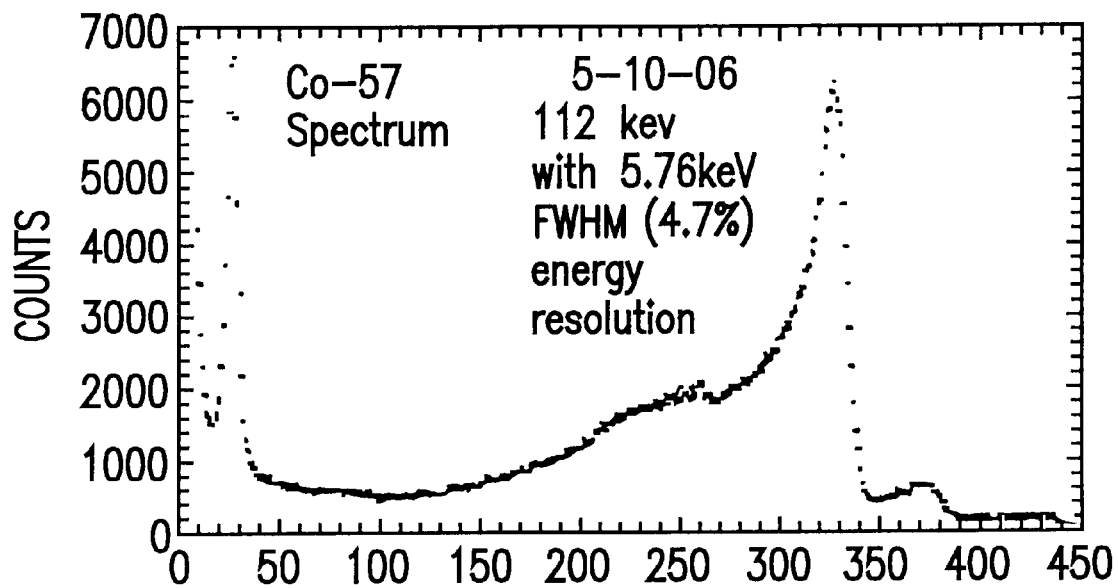
FIG. 9 is a graph illustrating the energy spectrum of Cobalt-57 using a CdZnTe detector.

The energy spectrum of a Cobolt-57 obtained by a 2 millimeter thick CdZnTe crystal is shown in FIG. 9. The low energy tail is clearly seen at higher energies.

In one embodiment of the invention, CdZnTe strip detectors produced from $Cd_{0.8}Zn_{0.2}Te$ wafers were used. The strip pitch was 1 millimeter with a total of 32 strips on each side, providing an active area of 3.2 centimeters by 3.2 centimeters. The strips on each side were orthogonal to each other in order to provide both the x and y dimensions for an interaction. The CdZnTe strip detectors can be from 1.5 to 2.5 millimeters thick. Two-dimensional arrays of CdZnTe pad detectors can also be used. Pad detectors generally provide better results than strip detectors since they do not have the positional ambiguity associated with strip detectors when there is more than one event simultaneously interacting with multiple detectors.

A full size cylindrical system according to the present invention was modeled using the MCNP Monte Carlo code discussed above. The internal and external radii of this cylindrical system were 15 and 50 centimeters, respectively. The length of the modeled system was 50 centimeters long. The phantom used at the center was a standard cylinder 20 centimeters in diameter 20 centimeters long filled with water and 1 $\mu$Ci/cc of a $^{99m}Tc$ radiotracer. Double-sided silicon strip detectors that were 1 millimeter thick with a 1 millimeter strip pitch were modeled in cylindrical form. All together, 36 planes were placed inside the detector with a 1 centimeter separation between planes. The total thickness of the 36 planes is 3.6 centimeters corresponding to a 72 percent Compton scatter probability. The 141 keV gamma rays, produced uniformly in all directions in the phantom, were tracked along their paths until they were fully absorbed or escaped through the back or sides of the detector. A 3 keV energy threshold of detection was imposed on each silicon detector. A calorimeter behind or at the sides of the model was not used.

Figure 10:
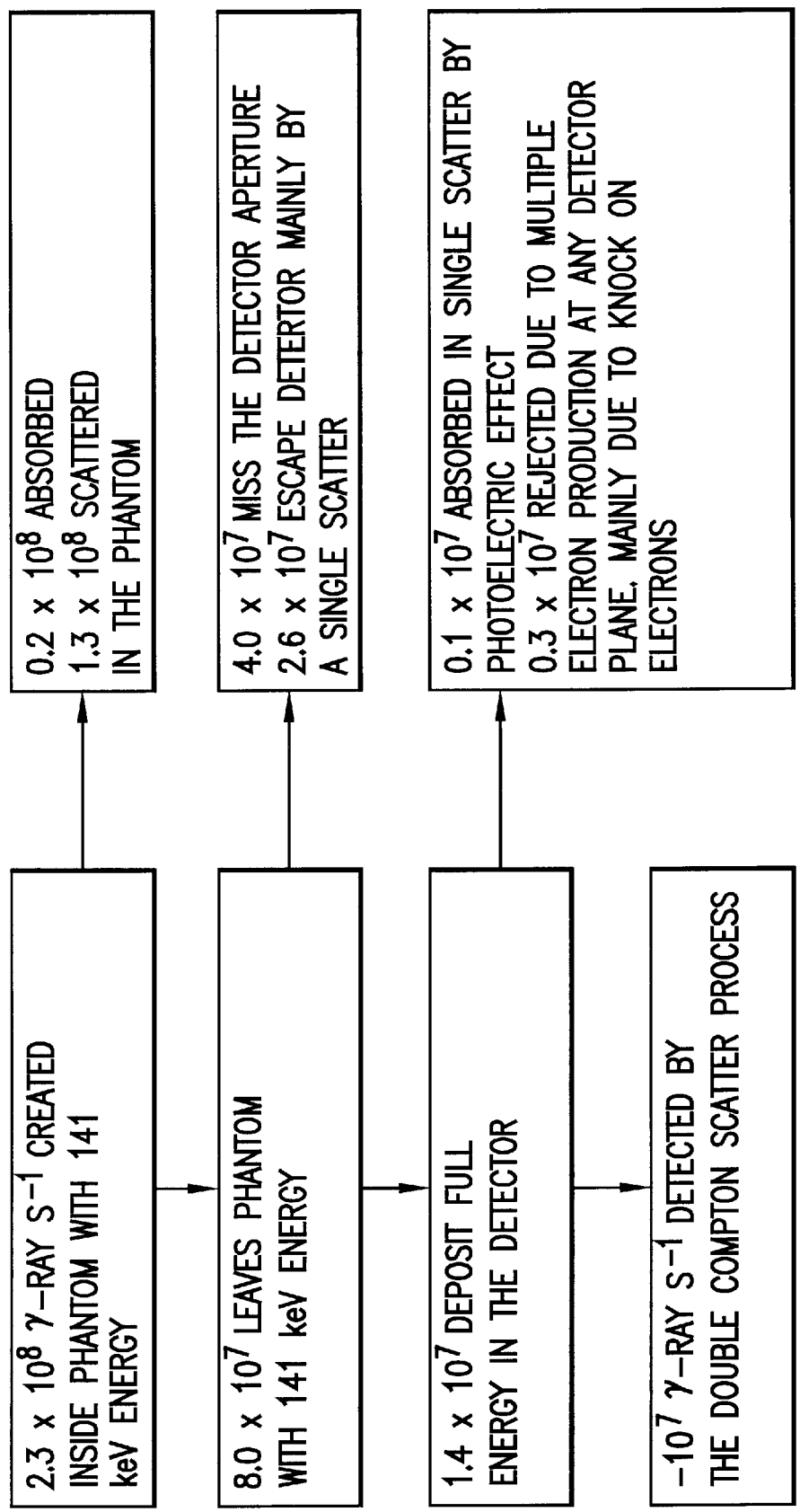
FIG. 10 is a flowchart outlining the Monte Carlo gamma ray history for a modeled system according to the invention.

The history of the 141 keV photon was traced by Monte Carlo calculations, the results of which are shown in FIG. 10. The Monte Carlo calculations were carried out for about 100,000 events and the results scaled to the simulated phantom. The 141 keV photons scattered in the phantom are effectively discriminated by the high energy resolution. This significantly reduces the major scattered photon background. The single scatter photons are rejected as their directions cannot be measured. The events which create multiple electrons in the same detector wafer are also rejected. Most of these are probably due to knock on electrons by the recoil electron. In most cases the secondary electrons are created and absorbed within the pixel size at the position of the interaction. These events are legitimate and can be used in imaging.

The forward and backscattered gamma ray events can be easily identified because of the strict relationship imposed by the Compton scatter formula. This is especially true at low photon energies. For 141 keV $^{99m}Tc$ gamma rays, the energies deposited in the interaction point nearest to the patient are limited to 0 to 31.5 keV and 110.5 to 90.9 keV for forward and back scattered photons (i.e., $\theta \leq 90°$), respectively. For the interaction point farthest from the patient (i.e., $90° \leq \theta \leq 180°$), the energies deposited are 31.5 to 50.1 keV and 141 to 110.5 keV for the forward and back scattered photons, respectively. Since the energy at each interaction plane is measured separately, such widely differing energy deposition for the forward and backward scattered photons is easily identifiable and the direction cones can be calculated. Therefore the backscattered events that deposit full energy in the detector are good events and can be used in imaging.

The point sensitivity is estimated to be about 1,500 Cts s$^{-1}$ $\mu$Ci$^{-1}$. The volume sensitivity of the simulated detector is about 500,000 Cts s$^{-1}$ cm$^{-1}$ found by dividing the good event rate, 1×10$^7$ cts s$^{-1}$, by the length of the phantom. The sensitivity of the invention strongly depends on the amount of silicon used and can be improved further by increasing the number of silicon detectors. The number of silicon strip detectors can also be decreased to reduce cost since the sensitivity is high and some sacrifice is affordable.

The FWHM uncertainty in the cone half-angle, $\Delta\theta$, due to a detector of finite energy resolution (FWHM), $\Delta E_{e1}$ and $\Delta E_{e2}$ at first and second scattering planes can be calculated using the Compton scatter formula:

$$\Delta\theta = \frac{mc^2}{E_\gamma^2 \sin\theta} \left\{ \Delta E_{e1}^2 + \left[ \frac{E_\gamma^2}{E_{\gamma 1}^2} - 1 \right]^2 \Delta E_{e2}^2 \right\}^{1/2}$$

where mc$^2$ is the electron rest energy (511 keV), $\theta$ is the Compton scatter angle, and $E_\gamma$ and $E_{\gamma 1}$ are the incident and scattered photon energies. Applying the formula, the energy resolution due to the statistical fluctuation for electrons stopped inside the silicon microstrip detectors varies from 1.3 percent at 100 keV to 0.75 percent at 350 keV. The electronics noise of the detector is about 2 keV. Therefore the total energy resolution is dominated by the electronics noise which is the same for both the converter and the calorimeter.

The angular resolution is calculated with an energy resolution of 2 keV (FWHM) where $\Delta\theta$ for forward scattered gamma rays (i.e., $\theta < 90°$) varies from 5° at a $\theta$ of 30° to about 3.2° at a $\theta$ of 70° for 141 keV ($^{99m}Tc$) incident photons. The same calculation carried out for 364 keV $^{131}I$ gamma rays gives angular resolutions of approximately 1° for a $\theta$ of between 20° and 90°. Thus the angular resolution improves significantly with an increase in the photon energy. Also the effects of amplifier noise are reduced as more electron-hole pairs are created by higher energy scattered electrons. At a distance of 20 centimeters these angular resolutions produce effectively 6 to 3.5 millimeter spatial resolutions for 141 keV gamma rays and 3.5 to 1.5 millimeter spatial resolutions for 364 keV gamma rays. At a distance of 2.5 centimeters the same energy gamma rays produce 2.2 to 1.4 millimeter spatial resolutions and 0.4 millimeter spatial resolutions, respectively.

The geometric angular resolution, $\Delta\theta_{Geom}$, gives the axis of the image cone and is dependent upon the silicon microstrip detector pixel size and the distance between the first two scatters. The FWHM value can be calculated similar to that for a collimator. Normally the geometric angular resolution is kept much smaller than the scatter angle variation which depends strongly on the energy resolution as shown above. It is easier to adjust the geometric angular resolution in a silicon microstrip detector as the strip or pixel pitch dimensions can be as small as 25 microns. The pixel size for the simulated model is 1 square millimeter.

The Monte Carlo analysis shows that about $1\times10^8$ photons per second out of $2.3\times10^8$ enter the detector as shown in FIG. 10. As noted above, the simulated detector has 36 cylindrical planes with an average area of approximately $10^4$ square centimeters and about 75 percent of the photons making an interaction (i.e., $7.5\times10^7$ photons per second). Assuming each silicon microstrip detector wafer has dimensions of 5 centimeters by 5 centimeters, the singles rate in each wafer is about 5,000 Cts/s. Such singles rates are not excessive for silicon microstrip detectors which produce about 20 nanosecond long pulses. The coincidence requirement further reduces the actual readout rate to about 670 per second. Therefore dead time per detector is not a problem. However, the total count rates of the whole detector will be high. This problem is solved by establishing high level parallelism in readout electronics for which the silicon microstrip detectors are highly suitable. One possible way is to divide the detector into many radial sections and read each section individually. If it is divided into 20 sections than readout rate at each section will be about 500 kHz which can be easily handled by a standard CAMAC data acquisition system. The data rate will be even smaller due to some loss of events at the edges when the photons scatter into adjacent sections. This will also reduce sensitivity somewhat unless such events can be recovered by the electronics. There is also a large number of channels to readout. This is solved by using high density ASIC chips directly connected to the microstrips. Chips which produce a trigger signal when there is valid data and connect the strip that contains information to the output can be used.

Figure 11:
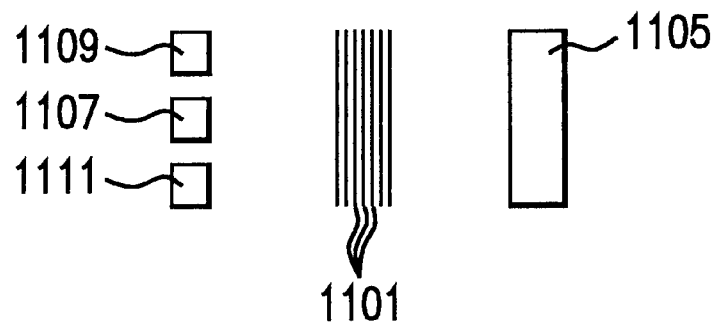
FIG. 11 is an illustration of a single head system according to the present invention.

FIG. 11 is an illustration of a simple, single head apparatus fabricated according to the present invention and used for system testing. The hodoscope is comprised of 10 layers 1101 of silicon strip detectors in which each detector layer 1101 has an area of 12.4 centimeters by 12.4 centimeters with a thickness of 1 millimeter. The distance between each layer 1301 is 0.5 centimeters. A calorimeter 1105 is symmetrically positioned 6 centimeters after the last hodoscope layer 1101. Calorimeter 1105 is a 2 millimeter thick CdTe detector with an area of 50 centimeters by 50 centimeters. A 141 keV gamma ray source 1107 with a 0.5 centimeter diameter is centrally positioned 10 centimeters above the first silicon plane 1101. A threshold energy of 10 keV was applied to the silicon strip detectors. An event is generated only if the incident gamma ray makes a Compton scatter in one of the silicon planes and also interacts at the calorimeter.

There were a total of 56,234 triggers out of 106 incident gamma rays. The low efficiency, about 5.6 percent, was due to the overall small silicon thickness of 1 cm (i.e., approximately 30 percent Compton scatter probability). The low efficiency was also a result of calorimeter 1105 not covering the sides of the hodoscope since most of the photons scattered at an angle of greater than 70° would not be detected. Lastly, since the thickness of calorimeter 1105 was only 2 millimeters, the absorption probability was approximately 85 to 50 percent for 90 to 131 keV scattered photons due to the Compton geometry. About 0.56 percent of the incident photons produced a photoelectric absorption inside the silicon hodoscope. The total number of events that deposited full energy in the detector was 4.2 percent. If the events are restricted to total absorption in calorimeter 1305 after Compton scattering once in the silicon hodoscope, about 2.8 percent of the incident photons were detected. This excludes totally absorbed events in silicon after 2 or more Compton scatters in the hodoscope.

Two more sources, 1109 and 1111, were added to the above single source discussed above. Source 1109 was positioned 2 centimeters from the center source in the –x direction while source 1111 was positioned 1.5 centimeters in the +x direction. All the sources produced 141 keV gamma rays sprayed into a cone the size of the hodoscope. The photons produced by the sources at the sides missed part of the detector aperture due to their position. Therefore, the strongest source imaged was the centrally placed one. The images were obtained using a standard analysis program. This program integrated the overlap of each event ring at the corresponding pixel. The energies deposited at the hodoscope and the calorimeter are randomly Gaussian distributed using the calculated energy resolutions for the preferred prototype system to simulate authentic spatial resolution.

The present Compton double scatter detectors provide two basic parameters for each event related to the incident photon direction; the scattered photon direction and the Compton scatter angle. The Direct Linear Algebraic Deconvolution (DLAD) technique can be used to analyze this information.

A concise explanation of the DLAD technique is provided below. The reconstruction of the source image from the Compton double scatter data can be represented by the following general formula:

$$D(\chi, \Psi, \varphi, E) = \int_{\chi, \Psi, E} I(\chi_0, \Psi_0, E') R(\chi, \Psi, \chi_0, \Psi_0, \varphi, E', E) d\chi_0 d\Psi_0 dE' + B(\chi, \Psi, \varphi, E)$$

In the above formula, $D(\chi, \Psi, \Phi, E)$ is the actual Compton scatter data observed by the detector in appropriate coordinates; $\chi$ and $\Psi$ are the coordinates of the rectangular image plane; $\Phi$ is the Compton scatter angle; E is the energy of the incident photon; $I(\chi_0, \Psi_0, E_0)$ is the true image of the source and is not a function of the Compton scatter angle; $R(\chi, \Psi, \chi_0, \Psi_0, \Phi, E', E)$ is the response function of the detector; and $B(\chi, \Psi, \Phi, E)$ is the gamma ray background. Normally the calculation is carried out for all energies within the detector sensitivity to determine the total gamma ray flux and for certain energy bands to obtain an energy spectrum. For application to the present invention, the energy spectrum is used to discriminate the scattered photon background. The calculation can also be done for different scatter angle bands. D and I are normally referred to as the data and the image spaces, respectively.

The response function in the DLAD technique is the concentric rings obtained by mapping the scattered photon direction vector in the image plane. This can be used as an ideal detector response function. The true detector response function, R, can be represented by $$R_{i\,j,\Phi_s}=\epsilon(E,\theta_j,\Phi_s)\cdot\Delta\Phi_s\cdot PSF\cdot G(\theta_i)$$

where i and j define the bins in the data and image spaces, respectively; $\Phi_s$ is the calculated Compton scatter angle as given by Compton scatter formula; $\epsilon$ is the detector efficiency; $\theta_i$ and $\theta_j$ are the incident zenith angles in data and image spaces, respectively; $\Delta\Phi_s$ is the scatter angle interval; PSF is the point spread function; and $G(\theta_i)$ is the geometric factor. The PSF is the distribution of the scattered photon vectors in the image plane. The PSF can be represented by the two dimensional normal distribution $$PSF=C(\theta_j,\Phi_s)e^{-\{[(\Phi_r-\Phi_s)^2]/[2\sigma^2(E)]\}}$$

where C is the normalization constant determined by the requirement that PSF×$G(\theta_i)$ is equal to 1. The PSF and $G(\theta_i)$ are symmetric in the azimuth, thus giving a two-dimensional image. The present invention can produce three-dimensional images due to the Compton scatter process. Therefore, either two-dimensional image slices parallel to the converter planes are produced or a direct three-dimensional image can be constructed.

The DLAD technique can produce fluctuations on the image space that are due to the geometric factor forcing data space to zero at the corners and edges of the field-of-view where the data may be scarce and the Poisson fluctuations are large. This effect can be improved by applying the positivity requirement. The positivity requirement is based on the fact that in image space one cannot get negative fluxes. The positivity constraint has been introduced into DLAD. The new technique is called Constrained Linear Algebraic Deconvolution (CLAD).

An important technological requirement for the present invention is a multichannel front end electronics (FEE) chip with self trigger output to readout the silicon strip and calorimeter detectors. A detailed description of a FEE chip is provided in U.S. Pat. No. 5,696,458, issued Dec. 9, 1997 and in co-pending U.S. patent application Ser. No. 08/866,117, filed Jun. 27, 1997, both disclosures of which are incorporated herein for all purposes.

Figure 12:
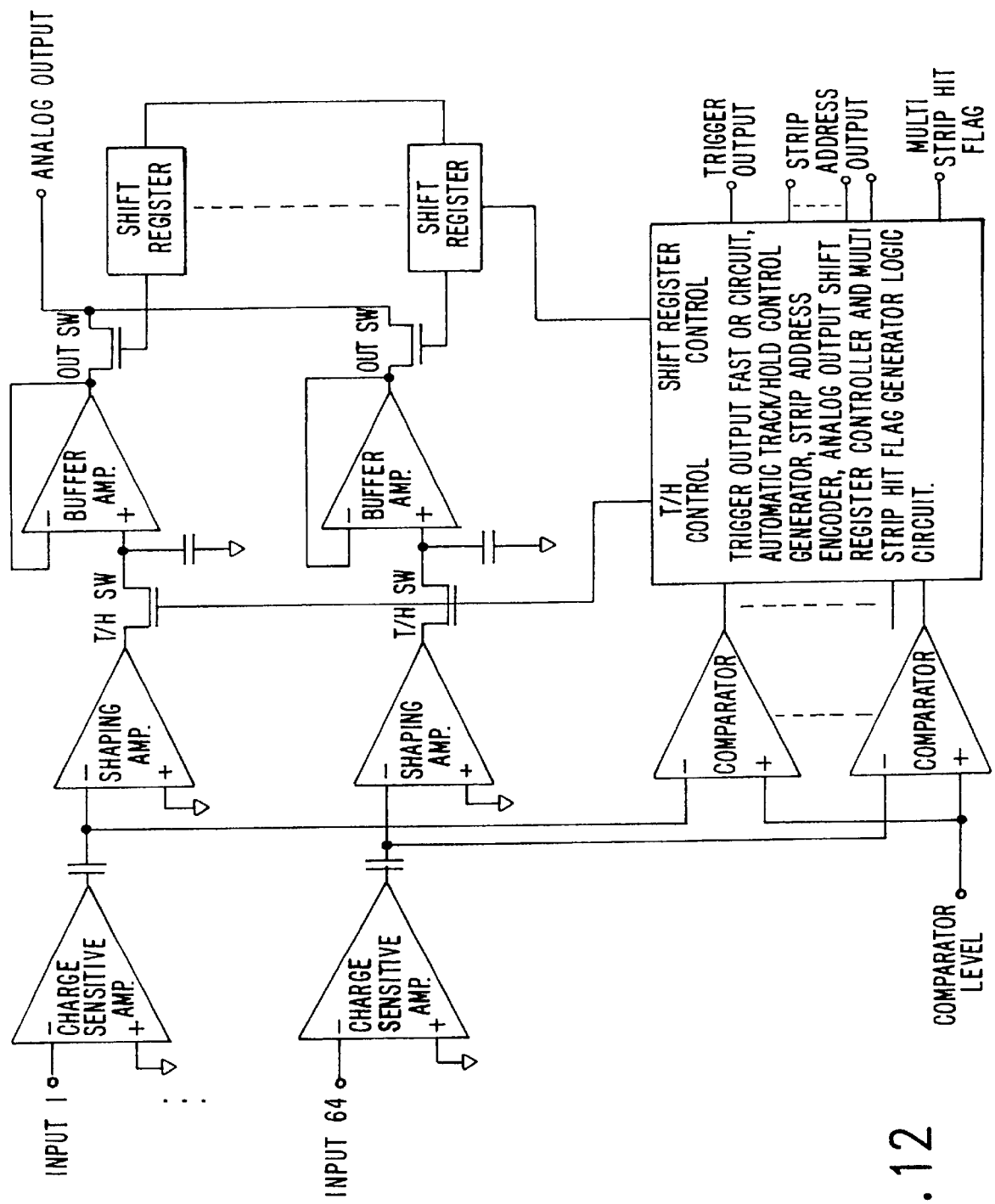
FIG. 12 is a schematic diagram of a possible multi-channel silicon microstrip detector readout chip with fast data readout and trigger output capability.

The preferred FEE chip is a 64 channel, charge sensitive, mixed signal ASIC CMOS chip, a version of which is illustrated in FIG. 12. Each channel of the chip consists of an analog section and a digital section. The input from the silicon strip detector is directly coupled to a low noise, charge sensitive amplifier. The outputs of the charge sensitive amplifier are connected to a shaper amplifier with a time constant of about 100 to 200 nanoseconds. The output of the shaper amplifier goes into the track and hold (T/H) switch. The T/H switch can be controlled externally or activated internally from the trigger output with a delay set to turn on the hold at the peak of the shaped pulse. The T/H switch is connected to the input of the buffer amplifier through the voltage following capacitor. When the T/H switch is open the voltage on the capacitor is held constant and the voltage level is buffered on to the analog output switch. A shift register connects each buffer output to the single analog output pin in sequence, from input 1 to N, by an external clock input. The shift register also has an external clear input to reset it and a clock output to daisy chain it to other readout chips. Only one clock input is sufficient if the clock outputs are connected in serial to the clock inputs of the adjacent readout chips. The charge sensitive amplifier outputs can be fanned out to comparators with a common external level adjustment. The outputs of the comparators can be fanned in through a fast OR circuit which will produce a trigger signal if any comparator input exceeds the set threshold. The trigger signal can also be used with a suitable delay to control the T/H switches to apply hold signal at the peak of the pulse from the shaper amplifier.

The data acquisition speed of the readout chip will also be increased using the extra versatility introduced by the comparators. The design shown in FIG. 12 does not tell which strip has the information so all strips are readout to find the strip that has the signal. A logic circuit can be added to the design which detects the channel with the largest signal from the comparator outputs, applies a track and hold signal, and connects the strip with the signal to the analog output pin. At the same time it can encode the address of the strip that has the information and output it as the address of the strip with the signal. There could be an occasional signal on more than one strip. Multi-hits can be detected and an output can be generated to warn of a multi-hit signal. The trigger signals are generated for each readout chip. They have to be externally processed for the hodoscope in coincidence with the calorimeter to produce the single trigger signal to activate the data acquisition system. For extremely high signal rates this may not be possible. In such a case each wafer or front end readout chip can be separately readout in parallel using independent data acquisition electronics and tagging each event time by using an accurate clock. The calorimeter crystals are also individually readout and event times tagged by the same clock. Since the calorimeter is running at much slower speeds, individual readout modules are not necessary and can be readout in groups.

The data readout can be carried out in parallel and can be stored on-board using individual module memory. This is the key to achieve fast data throughput rates. The data can be asynchronously accessed by the host computer, analyzed and displayed on screen in real time. Data acquisition rates of 1 to 10 MHz per readout chip (or silicon wafer) are achievable.

Figure 13:
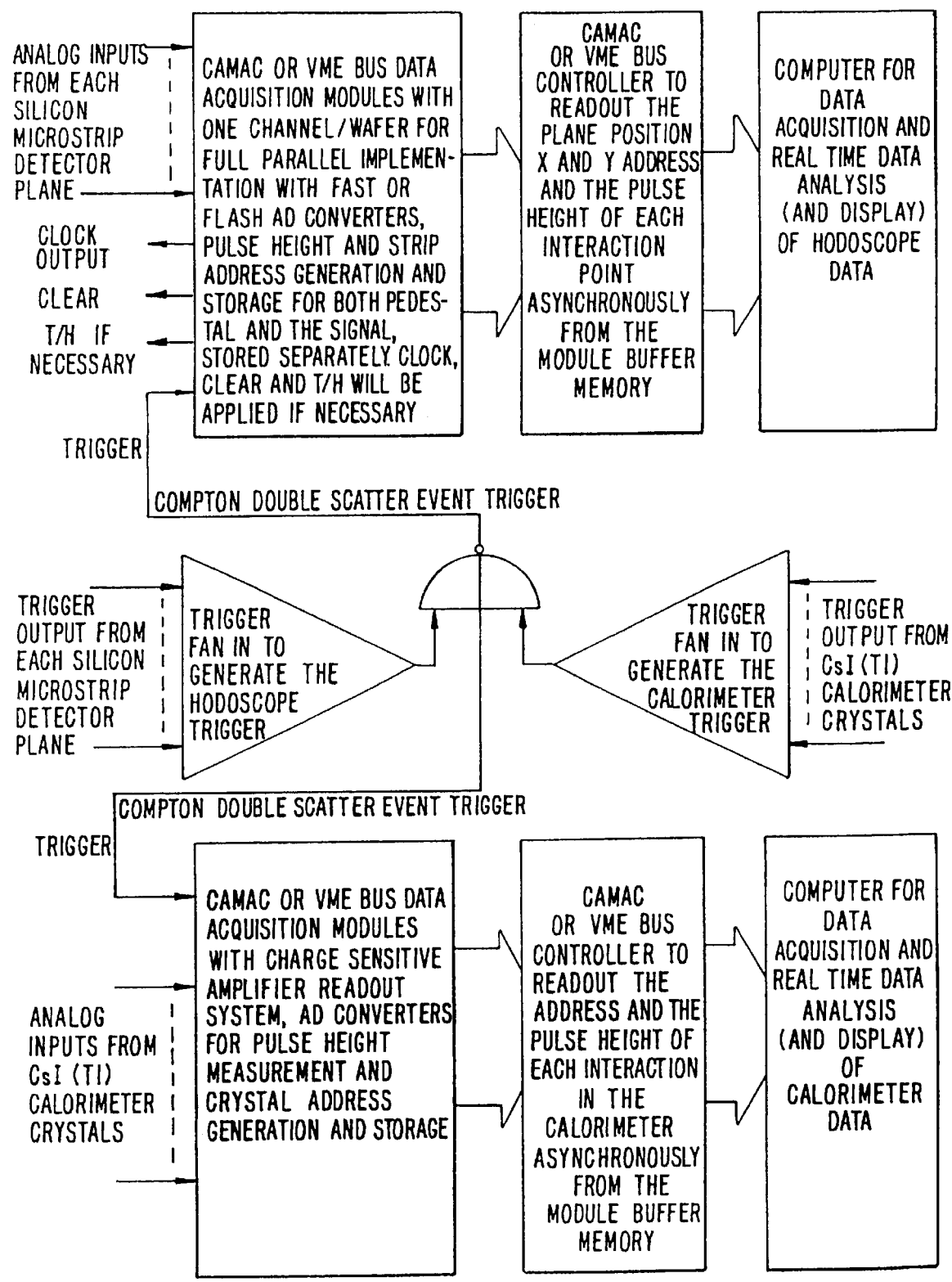
FIG. 13 is a block diagram of a real time data acquisition system for use with the present invention.

A block diagram of the readout electronics system is shown in FIG. 13. The electronics has two similar sections for the hodoscope and the calorimeter readout. A true event is a coincidence between the hodoscope and the calorimeter. The two master trigger signals from the hodoscope and the calorimeter are sent to a coincidence unit to create the Compton double scatter event trigger. The Compton double scatter trigger signal is only generated if there is a master trigger signal from both the hodoscope and the calorimeter. This is the arrangement which does not employ the time tagged data readout method. Time tagged data acquisition will only be used if absolutely necessary.

The Compton double scatter event trigger activates data acquisition for both the hodoscope and the calorimeter simultaneously. Either CAMAC or VME bus modules can carry out the data acquisition. The CAMAC system is the most cost effective. Faster computer interface busses such as Fastbus, VME or VXI bus can also be used. The custom designed data acquisition modules for the hodoscope will produce the necessary microstrip readout chip control electronics, such as the T/H (if not generated internally in the readout chip), a clear signal to reset the shift registers, and the clock pulse to multiplex each strip to the analog output.

The analog input channels from different hodoscope planes are read out synchronously with the clock pulse output. The module converts the pulse height information received from the analog output pin to a digital number. In parallel with reading the hodoscope data, it also digitizes the signal(s) from the calorimeter. Immediately after reading out the last signal it clears the hodoscope to reset the readout chip so that it can receive the next event. It is assumed that the analog output of each readout chip in each detector plane is fanned in to allow a single signal to be sent to the readout module. It is also possible to design a microstrip readout chip that can internally connect the strip which has the maximum signal to the analog output and also produce the encoded address of the strip. In such a case the clock output will not be necessary and the silicon microstrip detectors can be readout asynchronously at a much faster rate.

The custom made CAMAC modules are connected to the CAMAC crate controllers which are standard devices and available off the shelf. The controllers connect the modules to the data acquisition computer. Depending on the data rate and readout overhead, single or separate computers can be used to read the hodoscope and the calorimeter. The computer stores data on a hard disk, optical drive, or nonvolatile RAM depending on the application. If the data acquisition overhead is not high then one of the computers can analyze the data in real time or a separate computer can access the storage media asynchronously. The results of the data analysis are imaged onto the field-of-view through a display system in real time.

The data analysis techniques for nondestructive evaluation inspection resemble closely those of medical Computer Assisted Tomography (CAT) imaging. This type of imaging is based on the Radon transform and back projection techniques and is standard in the industry. New iterative techniques such as Maximum Likelihood and Maximum Entropy methods can also be applied to enhance the image quality as can the DLAD technique described above.

If a calorimeter is not used the direction and the energy of the incident photon has to be measured in the hodoscope. This can be achieved by increasing the total thickness. These measurements can be made by two scatters where the second scatter is a photoelectric absorption. If an incident photon makes 3 or more scatters (i.e., it is over determined), then the Compton scatter angle and the energy of the incident photon can be determined more than one independent way even if the photon does not deposit its full energy in the silicon converter and escape. Such multiple Compton scatters can also lead to a reduction in the azimuthal ambiguity (i.e., event ring) because the Compton scattered photon will be polarized and the third interaction position is dependent on the scattered photon direction.

Monte Carlo simulation of a hodoscope only system has been carried out using the same geometry as discussed above without a CdZnTe calorimeter and with 20 silicon strip detector planes. Out of $3 \times 10^6$ 141 keV gamma rays incident on the detector, 22 percent made a single scatter and escaped out, 10 percent of which were absorbed by the photoelectric effect. 7.7 percent of the incident gamma rays made two scatters, 20 percent of these depositing their full energy in the hodoscope. 4.2 percent of the incident gamma rays produced 3 or more scatters. Most of these, in theory, may be used to determine the incident photon energy and scatter angle.

If a pure single line source is used then a high sensitivity imaging mode can be applied with some reduction in spatial resolution. In this mode the background discrimination cannot be applied for double scatters. The requirement that the double scattered photon must deposit all of its energy in the hodoscope reduces the number of useful events for imaging by 80 percent. Since the energy of the incident photon is known than the missing energy of the escaped photon can be added to the second scatter and the scatter angle can be determined. This method improves the signal somewhat but also increases the background. However, for a hodoscope only system it may increase the good data rate by a significant factor.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method of imaging a portion of a human body, the method comprising the steps of:
    providing a radiopharmaceutical to said portion of said human body, said radiopharmaceutical producing gamma ray photons;
    positioning a detection system proximate to said portion of said human body, wherein said detection system is comprised of a hodoscope and a calorimeter, wherein said hodoscope is comprised of a plurality of detector planes;
    determining a direction and an energy for a portion of said gamma ray photons entering said detection system from a plurality of hodoscope output signals and from a plurality of calorimeter output signals;
    processing said direction and energy data for said portion of gamma ray photons; and
    displaying an image of said portion of said human body, wherein said image is based on said processed direction and energy data.

2. The method of claim 1, wherein said portion of said human body is an organ.

3. The method of claim 1, wherein said portion of said human body is a breast.

4. The method of claim 1, further comprising the step of positioning a shielding member around an entrance of said detection system, wherein said shielding member limits background gamma ray photons.

5. The method of claim 1, further comprising the steps of:
    positioning a second detection system proximate to said portion of said human body, wherein said second detection system is comprised of a second hodoscope and a second calorimeter, wherein said second hodoscope is comprised of a second plurality of detector planes;
    determining a second direction and a second energy for said portion of gamma ray photons entering said second detection system from a plurality of second hodoscope output signals and from a plurality of second calorimeter output signals;
    processing said second direction and second energy data for said portion of gamma ray photons; and
    displaying a three-dimensional image of said portion of said human body, wherein said image is based on said processed first and second direction data and said first and second energy data.

6. The method of claim 1, further comprising the steps of:
    repositioning said detection system proximate to said portion of said human body;
    determining a second direction and a second energy for said portion of gamma ray photons entering said detection system;
    processing said second direction and second energy data for said portion of gamma ray photons; and
    displaying a three-dimensional image of said portion of said human body, wherein said image is based on said processed first and second direction data and said first and second energy data.

7. The method of claim 1, wherein said processing step comprises applying a data analysis technique selected from the group consisting of a Radon transform and back projection technique, a Maximum Likelihood and Maximum Entropy technique, a Direct Linear Algebraic Deconvolution technique, and a Constrained Linear Algebraic Deconvolution technique.

8. The method of claim 1, wherein full energy of a gamma ray photon is determined by adding all of the energy deposited at said hodoscope and said calorimeter.

9. A medical imaging system for imaging a portion of a living organism, said portion treated with a radiopharmaceutical, said radiopharmaceutical emitting gamma ray photons, comprising:
a hodoscope comprised of a plurality of silicon detection planes, wherein an entrance aperture of said hodoscope is external to said living organism and proximate to said portion of said living organism, wherein emitted gamma ray photons pass into said hodoscope and are scattered within said hodoscope;
a multi-channel readout system coupled to said plurality of silicon detection planes;
a processor coupled to said multi-channel readout system; and
a monitor coupled to said processor, said monitor displaying an image of said portion of said living organism.

10. The medical imaging system of claim 9, wherein a portion of said emitted gamma ray photons undergo at least one Compton scatter within said plurality of silicon detection planes to yield a track direction corresponding to each of said portion of emitted gamma ray photons, wherein a total energy corresponding to each of said portion of said emitted gamma ray photons is absorbed within said plurality of silicon detection planes, and wherein said track direction and said total energy corresponding to each of said portion of emitted gamma ray photons is combined by said processor to generate said image.

11. The medical imaging system of claim 9, wherein a recoil electron is formed by a portion of said emitted gamma ray photons undergoing Compton scatter within said plurality of silicon detection planes, said recoil electron passing through a portion of said plurality of silicon detection planes, wherein a position of said recoil electron is recorded for each of said portion of said plurality of silicon detection planes.

12. The medical imaging system of claim 9, further comprising a calorimeter enclosing a portion of said hodoscope, wherein said calorimeter is coupled to said multi-channel readout system.

13. The medical imaging system of claim 12, wherein said scattered gamma ray photons passing through said hodoscope form recoil electrons during passage through said plurality of silicon detection planes, wherein said hodoscope determines a track direction by a first scatter vertex and an energy associated with said recoil electrons, wherein said scattered gamma ray photons are totally absorbed within said calorimeter, and wherein an energy of said absorbed gamma ray photons is determined by said calorimeter.

14. The medical imaging system of claim 12, further comprising a shielding member proximate to said hodoscope entrance aperture positioned to limit background gamma ray photons.

15. The medical imaging system of claim 12, wherein said calorimeter is selected from the group of calorimeter detector materials consisting of HPGe, BGO, $CdWO_4$, CsF, NaI(Tl), CsI(Na), CsI(Tl), CdTe, CdZnTe, $HgI_2$, GaAs, and $PbI_2$.

16. The medical imaging system of claim 12, wherein said calorimeter is comprised of CdZnTe detectors selected from the group consisting of CdZnTe strip detectors, CdZnTe pad detectors, and CdZnTe pixel detectors.

17. The medical imaging system of claim 12, wherein said calorimeter is comprised of CsI(Tl) crystals coupled to PIN photodiodes.

18. The medical imaging system of claim 12, wherein said calorimeter is comprised of multiple calorimetry layers.

19. The medical imaging system of claim 12, wherein said portion of said hodoscope enclosed by said calorimeter is a side portion.

20. The medical imaging system of claim 12, wherein said portion of said hodoscope enclosed by said calorimeter is a back portion, wherein said back portion is opposed to said hodoscope entrance aperture.

21. The medical imaging system of claim 12, further comprising a slot collimator proximate to said hodoscope entrance aperture.

22. The medical imaging system of claim 9, wherein said radiopharmaceutical is selected from the group consisting of thallium-201, technetium-99m, iodine-123, iodine-131, and fluorine-18.

23. The medical imaging system of claim 9, wherein said plurality of silicon detection planes is selected from the group consisting of silicon microstrip detectors, silicon strip detectors, silicon pad detectors, silicon pixel detectors, double sided silicon microstrip detectors, and double sided silicon strip detectors.

24. The medical imaging system of claim 9, wherein said plurality of silicon detection planes have a predetermined orientation with respect to said entrance aperture, said predetermined orientation selected from the group consisting of parallel, perpendicular, or an angle.

25. The medical imaging system of claim 9, wherein each of said plurality of silicon detection planes is comprised of at least two bridged silicon detectors, wherein said silicon detectors are selected from the group consisting of strip and microstrip detectors.

26. The medical imaging system of claim 9, wherein each of said plurality of silicon detection planes has a corresponding thickness within a range of about 100 micrometers to about 5 millimeters.

27. The medical imaging system of claim 9, wherein said plurality of silicon detection planes are separated by a distance of between about 0.2 and 2 centimeters.

28. The medical imaging system of claim 9, wherein said plurality of silicon detection planes is between 10 and 25 silicon detection planes.

29. The medical imaging system of claim 9, said processor applying a data analysis technique selected from the group consisting of a Radon transform and back projection technique, a Maximum Likelihood and Maximum Entropy technique, a Direct Linear Algebraic Deconvolution technique, and a Constrained Linear Algebraic Deconvolution technique.

30. The medical imaging system of claim 9, wherein said emitted gamma ray photons have an energy within a range of about 40 keV to about 2,000 keV.

31. The medical imaging system of claim 9, wherein said multi-channel readout system is comprised of ASIC chips, wherein said plurality of silicon detection planes is comprised of silicon strip detectors, and wherein said strips are fanned in to match a chip bonding pitch corresponding to said ASIC chips.

32. The method of claim 9, wherein full energy of a gamma ray photon is determined by adding all of the energy deposited at the hodoscope and a calorimeter.

* * * * *